United States Patent
Lee et al.

(10) Patent No.: US 10,195,100 B2
(45) Date of Patent: Feb. 5, 2019

(54) FIXING MODULE AND MOTION ASSISTANCE APPARATUS INCLUDING THE SAME

(71) Applicant: Samsung Electronics Co., Ltd., Suwon-Si, Gyeonggi-Do (KR)

(72) Inventors: Minhyung Lee, Anyang-si (KR); Youn Baek Lee, Yongin-si (KR); Jeonghun Kim, Hwaseong-si (KR); Se-gon Roh, Suwon-si (KR); Jongwon Lee, Uiwang-si (KR); Byungjune Choi, Gunpo-si (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 961 days.

(21) Appl. No.: 14/575,533

(22) Filed: Dec. 18, 2014

(65) Prior Publication Data

US 2016/0045387 A1    Feb. 18, 2016

(30) Foreign Application Priority Data

Aug. 18, 2014  (KR) .................. 10-2014-0107171

(51) Int. Cl.
*A61H 3/00* (2006.01)
*A61H 1/02* (2006.01)
(Continued)

(52) U.S. Cl.
CPC .......... *A61H 3/008* (2013.01); *A61F 5/0193* (2013.01); *A61F 5/02* (2013.01); *A61F 5/022* (2013.01);
(Continued)

(58) Field of Classification Search
CPC ........ A61H 1/0024; A61H 3/00; A61H 3/008; A61F 5/02–5/028; B25J 9/0006
See application file for complete search history.

(56) References Cited

U.S. PATENT DOCUMENTS

| | | | | | |
|---|---|---|---|---|---|
| 2,327,207 | A | * | 8/1943 | Necomer et al. | ......... A41F 9/02 2/237 |
| 4,523,337 | A | * | 6/1985 | Leibowitz | ................ A41B 9/14 2/237 |

(Continued)

FOREIGN PATENT DOCUMENTS

| | | |
|---|---|---|
| CN | 1444468 A | 9/2003 |
| CN | 201085760 Y | 7/2008 |

(Continued)

OTHER PUBLICATIONS

Extended European Search Report issued by the European Patent Office dated Aug. 5, 2016 for corresponding EP Patent Application No. 15152670.4.

(Continued)

*Primary Examiner* — Valerie L Woodward
(74) *Attorney, Agent, or Firm* — Harness, Dickey & Pierce, P.L.C.

(57) ABSTRACT

Provided are a fixing module and a motion assistance apparatus including the fixing module including a first side frame including a first central portion on one side of a user, a first front extending portion configured to extend from the first central portion along a front side of the user, and a first rear extending portion configured to extend from the first central portion along a rear side of the user, and a second side frame including a second central portion on another side of the user, a second front extending portion configured to extend from the second central portion along the front side of the user, and a second rear extending portion.

28 Claims, 11 Drawing Sheets

(51) Int. Cl.
*A61F 5/02* (2006.01)
*B25J 9/00* (2006.01)
*A61F 5/01* (2006.01)

(52) U.S. Cl.
CPC ........... *A61F 5/028* (2013.01); *A61H 1/0244* (2013.01); *B25J 9/0006* (2013.01); *A61F 2005/0137* (2013.01); *A61F 2005/0155* (2013.01); *A61H 2003/007* (2013.01)

(56) References Cited

U.S. PATENT DOCUMENTS

| | | | | |
|---|---|---|---|---|
| 5,020,790 | A * | 6/1991 | Beard | A61F 5/0102 482/4 |
| 5,830,168 | A | 11/1998 | Finnell et al. | |
| 7,416,538 | B2 | 8/2008 | Katoh et al. | |
| 7,780,616 | B2 | 8/2010 | Katoh et al. | |
| 8,474,672 | B1 * | 7/2013 | Keith | B25J 9/0006 224/576 |
| 8,652,075 | B2 | 2/2014 | Takahashi et al. | |
| 2006/0064047 | A1 * | 3/2006 | Shimada | A61F 5/0102 602/23 |
| 2006/0258967 | A1 * | 11/2006 | Fujil | A61F 5/0102 602/23 |
| 2007/0010378 | A1 * | 1/2007 | Katoh | A61F 5/0102 482/105 |
| 2007/0056592 | A1 * | 3/2007 | Angold | A61H 3/00 128/845 |
| 2012/0316476 | A1 * | 12/2012 | Shimizu | A61H 1/0244 601/35 |
| 2012/0316477 | A1 * | 12/2012 | Hamaya | H01M 2/1066 601/35 |
| 2013/0197408 | A1 * | 8/2013 | Goldfarb | A61F 5/0102 601/35 |
| 2014/0121578 | A1 | 5/2014 | Wu | |
| 2014/0276263 | A1 * | 9/2014 | Caires | A61H 3/00 601/34 |
| 2016/0331625 | A1 * | 11/2016 | Sankai | B25J 9/0006 |

FOREIGN PATENT DOCUMENTS

| | | |
|---|---|---|
| CN | 101316567 A | 12/2008 |
| CN | 101808604 A | 8/2010 |
| CN | 102499859 A | 6/2012 |
| EP | 2189136 A1 | 5/2010 |
| FR | 2350120 A1 | 12/1977 |
| JP | 2009284919 A | 12/2009 |
| JP | 2012254237 A | 12/2012 |
| JP | 5411003 B2 | 2/2014 |
| KR | 100598504 B1 | 7/2006 |
| KR | 100612031 B1 | 8/2006 |
| KR | 100953674 B1 | 4/2010 |
| KR | 101142240 B1 | 5/2012 |
| KR | 101146112 B1 | 5/2012 |
| WO | WO-2013/070253 A1 | 5/2013 |
| WO | WO-2013-188868 A1 | 12/2013 |

OTHER PUBLICATIONS

Partial European Search Report for EP 15152670 dated Feb. 4, 2016.

Office Action issued by the Chinese Patent Office dated May 22, 2018 for the corresponding CN Patent Application No. 201510099047.2.

* cited by examiner

20

FIXING MODULE AND MOTION ASSISTANCE APPARATUS INCLUDING THE SAME

CROSS-REFERENCE TO RELATED APPLICATION

This application claims the priority benefit of Korean Patent Application No. 10-2014-0107171, filed on Aug. 18, 2014, in the Korean Intellectual Property Office, the disclosure of which is incorporated herein by reference in its entirety.

BACKGROUND

1. Field

Example embodiments relate to a fixing module and/or a motion assistance apparatus including the same.

2. Description of the Related Art

With the onset of an aging society, an increased number of people may experience inconvenience and/or pain from joint problems. Therefore, there is increased interest in motion assistance apparatuses that may enable the elderly or patients with joint problems to walk with less effort. The motion assistance apparatuses may include active joint structures including hydraulic systems and/or driving motors to drive each joint portion to improve muscular strength of legs of users. However, conventionally a motion assistance apparatus may come in various fixed sizes according to a waist of the user. Further, conventionally, a motion assistance apparatus may shake due to torsional forces applied thereto while assisting the user with walking.

SUMMARY

At least one example embodiment relates to a fixing module.

According to some example embodiments, the fixing module may include a first side frame including a first central portion on one side of a user, a first front extending portion configured to extend from the first central portion along a front side of the user, and a first rear extending portion configured to extend from the first central portion along a rear side of the user, and a second side frame including a second central portion on another side of the user, a second front extending portion configured to extend from the second central portion along the front side of the user, and a second rear extending portion configured to extend from the second central portion along the rear side of the user. The first central portion and the second central portion may be disposed to face each other, and a distance between the first central portion and the second central portion may be adjustable.

Example embodiments provide that the first front extending portion and the second front extending portion may be detachable, and the first rear extending portion and the second rear extending portion may be detachable.

Example embodiments provide that an overlapping area of the first front extending portion and the second front extending portion may be adjustable.

Example embodiments provide that the first front extending portion may include a binding portion configured to be bound to the second front extending portion, and a connecting portion configured to rotatably connect the binding portion to the first central portion.

Example embodiments provide that an overlapping area of the first rear extending portion and the second rear extending portion may be adjustable.

Example embodiments provide that the first rear extending portion may be configured to slide with respect to the second rear extending portion.

Example embodiments provide that the fixing module further includes a fastening member configured to penetrate through a first guide hole and a second guide hole to prevent relative movements of the first rear extending portion and the second rear extending portion. The first rear extending portion may include the first guide hole, and the second rear extending portion may include the second guide hole corresponding to the first guide hole.

Example embodiments provide that at least one of the first side frame and the second side frame may further include a supporting member configured to extend from a rear extending portion of the at least one side frame in a direction.

Example embodiments provide that the first side frame may further include a first upper supporting member configured to extend from the first rear extending portion in an upward direction, the second side frame may further include a second upper supporting member configured to extend from the second rear extending portion in an upward direction, and the first upper supporting member and the second upper supporting member may be disposed on both sides based on a spine of the user, respectively, to support erector spinae muscles of the user.

Example embodiments provide that the first side frame may further include a first lower supporting member configured to extend from the first rear extending portion toward a lower side, the second side frame may further include a second lower supporting member configured to extend from the second rear extending portion toward the lower side, and the first lower supporting member and the second lower supporting member may be disposed to support hip muscles of the user.

Example embodiments provide that the supporting member may include a plate disposed to be orthogonal to a longitudinal direction of the rear extending portion, and a plurality of protruding portions configured to protrude from the plate.

Example embodiments provide that the plurality of protruding portions may be disposed to be spaced apart from one another in a longitudinal direction of the plate.

Example embodiments provide that the supporting member may further include a stiffener configured to penetrate through the plurality of protruding portions.

Example embodiments provide that the supporting member may include a plate disposed to be orthogonal to a longitudinal direction of the rear extending portion, and a stiffener of which portions to be disposed at both end portions of the plate are to be fixed, and of which a portion to be disposed at a central portion of the plate is to be unfixed.

Example embodiments provide that the supporting member may include a plate disposed to be orthogonal to a longitudinal direction of the rear extending portion, and a stiffening wire configured to be embedded at an end portion of the plate in a width direction of the plate, and to extend in a longitudinal direction of the plate.

Example embodiments provide that the supporting member may be provided to have a length longer than a width, and a stiffness of both end portions of the supporting member may be greater than a stiffness of a central area of the supporting member in a longitudinal direction of the supporting member.

According to other example embodiments, the fixing module may include a first side frame configured to cover one side surface of a user, and of which both end portions are configured to extend along a front surface and a rear surface of the user, a second side frame configured to cover another side surface of the user, and of which both end portions are configured to extend along the front surface and the rear surface of the user, and a supporting member to which the first side frame and the second side frame are slidingly connected, and configured to support the rear surface of the user.

Example embodiments provide that a front end portion of the first side frame and a front end portion of the second side frame may be configured to be detachable from each other, and a rear end portion of the first side frame and a rear end portion of the second side frame may be respectively configured to be detachable from the supporting member.

At least one example embodiment relates to a motion assistance apparatus.

According to an example embodiment, the motion assistance apparatus may include a fixing module including a first separable frame on one side surface of a user, and a second separable frame on another side surface of the user, a distance between the first separable frame and the second separable frame being adjustable, a driving module provided in the fixing module, and a joint assembly configured to rotate by the driving module, and assist a rotary motion of a joint portion of the user.

Example embodiments provide that the first separable frame and the second separable frame may include a flexible material, the fixing module may further include an upper supporting member and a lower supporting member configured to extend toward an upper side and a lower side of the user, respectively, and the upper supporting member may be configured to pressurize the upper side of the user when the joint assembly rotates in a direction, and the lower supporting member may be configured to pressurize the lower side of the user when the joint assembly rotates in another direction.

In some example embodiments, the motion assistance apparatus may include a fixing device configured to attach to a waist of a wearer thereof, the fixing module including a plurality of interlocking frames separated by a distance, the fixing device configured to adjust the distance between the interlocking frames to secure the motion assistance apparatus onto a waist of the wearer; a plurality of attachment devices configured to attach to thighs of the wearer; and a plurality of joint assemblies mounted to respective ones of the plurality of side frames, the joint assemblies configured to apply a torque to the plurality of attachment devices to assist the user with movement of their hip joints.

In some example embodiments, the plurality of interlocking frames includes a first interlocking frame and a second interlocking frame, the first interlocking frame configured detach from the second interlocking frame to allow the user to remove the fixing device.

In some example embodiments, the plurality of interlocking frames include rear portions configured to contact a respective side of a lower back of the wearer and front portions configured to contact a respective side of a lower abdomen of the wearer, and a first one of the rear portions and the front portions of the plurality of interlocking frames is configured to allow a fastening member to penetrate through a guide slot therein to allow a first one of the plurality of interlocking frames to slide relative to a second one of the plurality of interlocking frames; and a second one of the rear portions and the front portions of the plurality of interlocking frames include a clasp configured to selectively fasten the first interlocking frame to the second interlocking frame.

In some example embodiments, the fixing device includes a supporting device extending in one or more of a cranial or caudal direction from the fixing device, the supporting device configured to offset a torsional force generated when the plurality of joint assemblies applies the torque to the attachment devices.

In some example embodiments, the supporting device has a shape such that a stiffness of the supporting device decreases towards distal ends thereof.

In some example embodiments, the fixing device is configured to adjust the distance between the plurality of interlocking frames in a first direction and move the supporting device in a second direction perpendicular to the first direction.

In some example embodiments, the plurality of interlocking frames are symmetric with respect to the supporting device.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of some of the example embodiments, taken in conjunction with the accompanying drawings of which.

DETAILED DESCRIPTION

Figure 1:
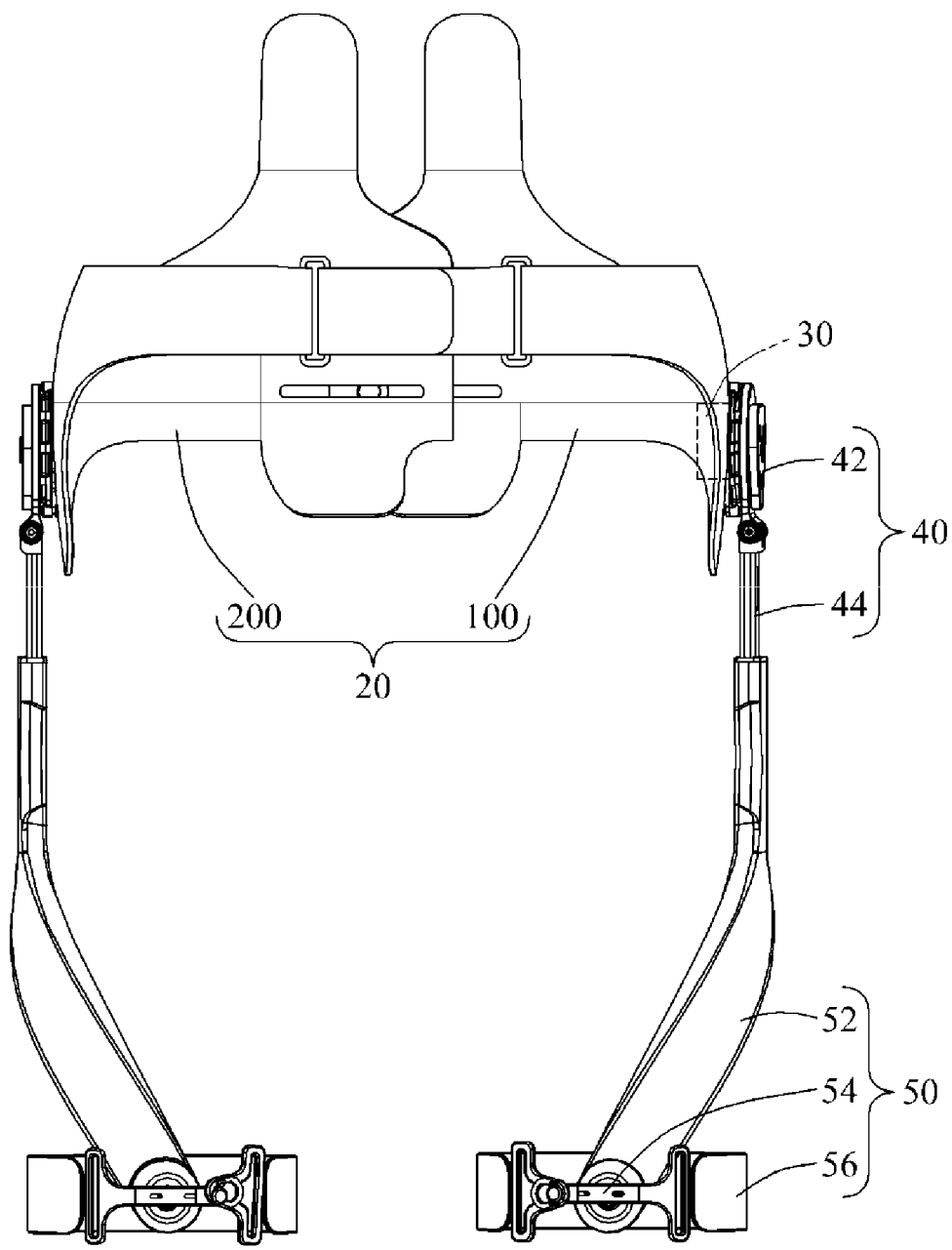
FIG. 1 is a front view illustrating a motion assistance apparatus according to some example embodiments.

Some example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present.

In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, some which are illustrated in the accompanying drawings, wherein like reference numerals may refer to like components throughout.

Figure 2:
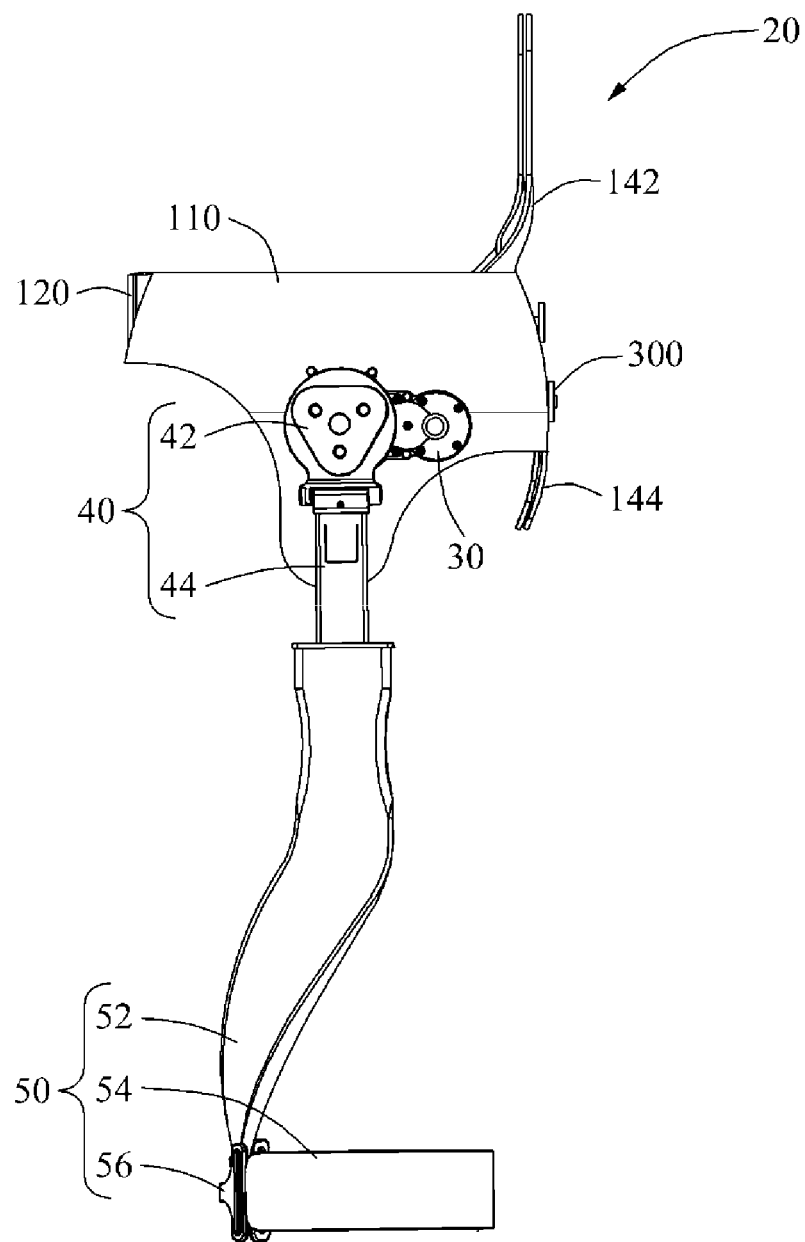
FIG. 2 is a side view illustrating a motion assistance apparatus according to some example embodiments.

FIG. 1 is a front view illustrating a motion assistance apparatus according to some example embodiments, and FIG. 2 is a side view illustrating the motion assistance apparatus according to some example embodiments.

Referring to FIGS. 1 and 2, a motion assistance apparatus 10 may be worn by a user to assist a motion of the user.

The user may correspond to a human, an animal, or a robot. However, the user is not limited thereto. In addition, although FIG. 1 illustrates a case in which the motion assistance apparatus 10 assists motions of thighs of the user, the motion assistance apparatus 10 may also assist a motion of an upper body, for example, a hand, an upper arm, and a lower arm of the user. Further, the motion assistance apparatus 10 may assist a motion of another part of a lower body, for example, a foot, and a calf of the user. The motion assistance apparatus 10 may assist a motion of a part of the user.

Hereinafter, a case in which the motion assistance apparatus 10 assists motions of thighs of a human will be described. However, example embodiments are not limited thereto.

The motion assistance apparatus 10 may include a fixing module 20, a driving module 30, a joint assembly 40, and a supporting module 50.

The fixing module 20 may be fixed to the user. The fixing module 20 may be provided in a form of covering an outer surface of the user. For example, the fixing module 20 may be fixed to the sides of a waist of the user, and include a curved surface corresponding to a contact portion of the user. The fixing module 20 includes a first side frame 100 disposed on one side of the waist of the user, and a second side frame 200 disposed on another side of the waist of the user.

The driving module 30 may provide power that is transmitted to the joint assembly 40. For example, the driving module 30 may be disposed in a lateral direction of the joint assembly 40, in detail, such that an axis of rotation of the diving module 30 may be spaced apart from an axis of rotation of the joint assembly 40. Therefore, when compared to a case in which the driving module 30 and the joint assembly 40 share an axis of rotation, a protruding height from the user may relatively decrease. In other example embodiments, the driving module 30 may be more spaced apart from the joint assembly 40. Therefore, a power transmitting module may be additionally provided to transmit power from the driving module 30 to the joint assembly 40. The power transmitting module may be a rotary body such as, for example, a gear, or a longitudinal member such as, for example, a wire, a cable, a string, a rubber band, a spring, a belt, and a chain.

The joint assembly 40 may receive power from the driving module 30, and assist a motion of a joint portion of the user. The joint assembly 40 may be disposed on one side of the fixing module 20 at a position corresponding to the joint portion of the user, for example, at a hip joint of the user. One side of the joint assembly 40 may be connected to the driving module 30, and another side of the joint assembly 40 may be connected to the supporting module 50.

The joint assembly 40 includes a rotating member 42, and a connecting member 44. The rotating member 42 may rotate using power received from the driving module 30. For example, the rotating member 42 may be disposed on one side of the hip joint of the user. The connecting member 44 may connect the rotating member 42 to the supporting module 50, and rotate using torque of the rotating member 42. The connecting member 44 may be provided, for example, in a hinge connection structure. By a hinge axis of the hinge connection structure and an axis of rotation of the rotating member 42, the supporting module 50 may perform a two degree of freedom (DOF) motion with respect to the fixing module 20.

The supporting module 50 may support a portion of the user, and assist a motion of the portion of the user. The supporting module 50 may be configured to rotate using torque of the joint assembly 40. The supporting module 50 may include a supporting frame 52, an applying member 54, and a supporting band 56.

The supporting frame 52 may transmit force to a portion of the user, for example, to the thighs of the user to assist the user in rotating their hip joints. One end portion of the supporting frame 52 may be rotatably connected to the joint assembly 40, and another end portion of the supporting frame 52 may be connected to the supporting band 56 to transmit force to a portion of the user. For example, the supporting frame 52 may push or pull a thigh of the user. The supporting frame 52 may extend and be bent in a longitudinal direction of the thigh of the user to cover at least a portion of the circumference of the thigh of the user. The one end portion of the supporting frame 52 may be disposed on a side surface of the thigh of the user, and the other portion of the supporting frame 52 may be disposed on a front surface of the thigh of the user. A surface on the side of the one end portion of the supporting frame 52 may be orthogonal to a surface on the side of the other end portion of the supporting frame 52.

The supporting frame 52 may be movably connected to the connecting member 44. By relative motions of the supporting frame 52 and the connecting member 44, a total length from the joint assembly 40 to the supporting band 56 may be variable. In this example, the supporting module 50 may perform a three degree of freedom (DOF) motion with respect to the fixing module 20.

The applying member 54 may be connected to the other end portion of the supporting frame 52 to apply force to a portion of the user. For example, the applying member 54 may be disposed along the front surface of the thigh of the user, or in a circumferential direction of the thigh of the user to push or pull the thigh of the user. The applying member 54 may include a curved surface corresponding to the thigh of the user, and configured to extend from the other end portion of the supporting frame 52 toward both sides of the supporting frame 52.

The supporting band 56 may be connected to one side of the applying member 54. For example, the supporting band 56 may be disposed to cover a circumference of at least a portion of the thigh of the user, thereby preventing separation between the thigh of the user and the supporting frame 52.

Figure 3:
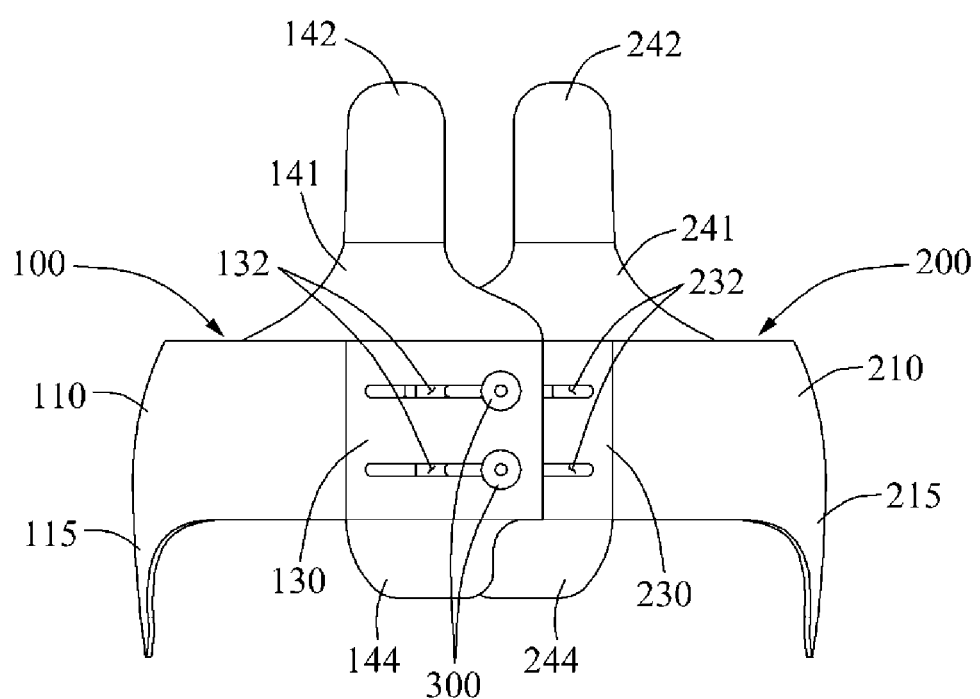
FIG. 3 is a rear view illustrating a fixing module according to some example embodiments.
Figure 4:
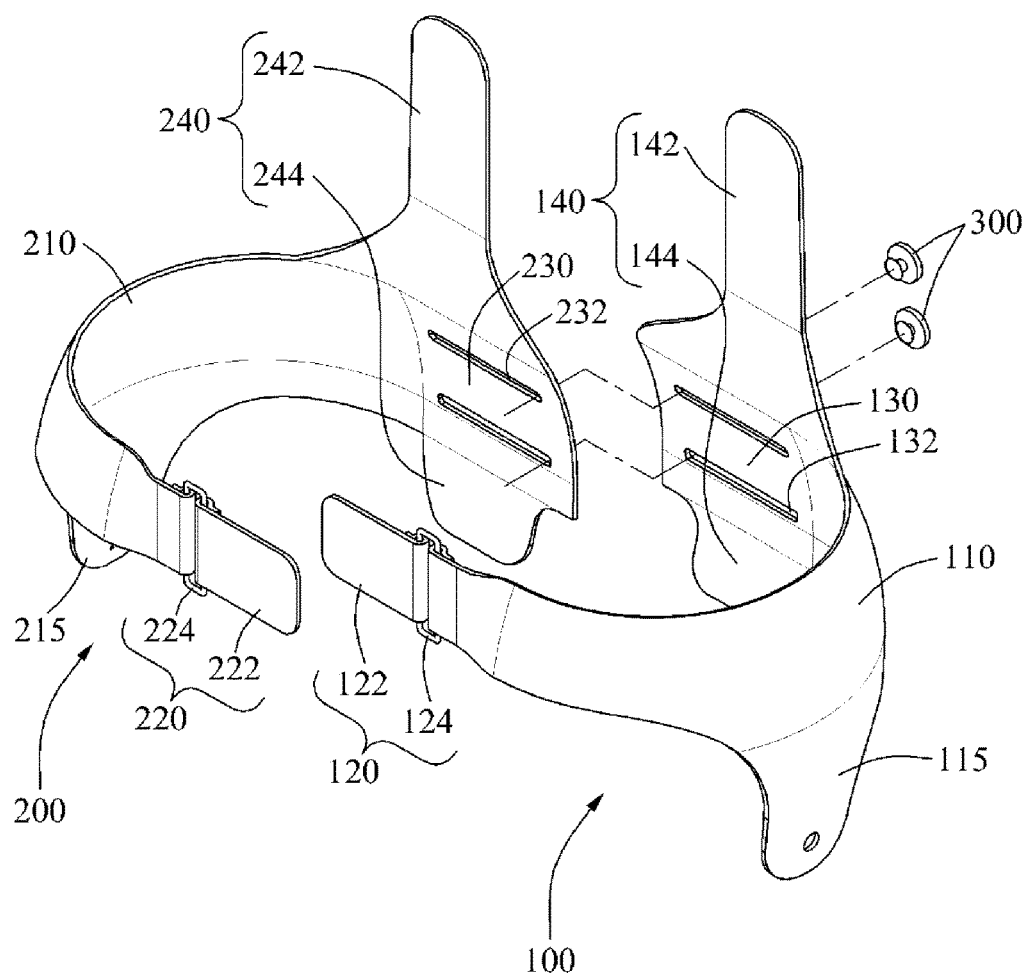
FIG. 4 is an exploded perspective view illustrating a fixing module according to some example embodiments.

FIG. 3 is a rear view illustrating a fixing module according to some example embodiments, and FIG. 4 is an exploded perspective view illustrating a fixing module according to some example embodiments.

Referring to FIGS. 3 and 4, the fixing module 20 may include the first side frame 100, the second side frame 200, and a fastening member 300. As discussed above, the first side frame 100 and the second side frame 200 may be configured to attach to opposite sides of the waist of the user. The first side frame 100 and the second side frame 200 may be connected to each other to form a single closed curve, for example, around the waist of the user.

The first side frame 100 and the second side frame 200 may be detachable from each other. Therefore, the first side frame 100 and the second side frame 200 may also be referred to as a "first separable frame" and a "second separable frame", respectively.

The first side frame 100 may cover one side surface of the waist of the user, a portion of a front surface of the waist of the user, and a portion of a rear portion of the waist of the user. For example, the first side frame 100 may fit around half of the pelvis of the user. The first side frame 100 may be provided roughly in a U-shape. The first side frame 100 may be provided using a relatively thin board. The first side frame 100 may be provided using a flexible material to improve a degree of contact with the user. In this example, the first side frame 100 may be deformed based on a shape of the user to be in close contact with the user. The first side frame 100 includes a first central portion 110, a first front extending portion 120, and a first rear extending portion 130.

The first central portion 110 may include a curved surface corresponding to one side surface of the user, and be disposed on the one side surface of the user. The first central portion 110 includes a joint mounting portion 115 configured to extend toward a hip joint portion of the user. The joint mounding portion 115 may be provided to cover the hip joint portion. The rotating member 42 of FIG. 1 may be provided on the joint mounting portion 115.

The first front extending portion 120 may extend from the first central portion 110 to cover at least a portion of the front surface of the user. The first front extending portion 120 may be provided to be detachable from the second side frame 200. For example, the first front extending portion 120 includes a first binding portion 122, and a first connecting portion 124.

The first binding portion 122 may be provided to be detachable from the second side frame 200. For example, the first binding portion 122 may include a base plate having a shape of a board, and a hook and loop fastener provided on the base plate. The first binding portion 122 may also be fastened with the second side frame 200 in a structure of a buckle. However, the shape of the first binding portion 122 is not limited thereto. For example, the first and second binding portions 122, 22 may be series of buttons, tabs or posts that are adjustable, and/or form an adjustable belt like loop that is secured via pressure provided thereto. Further, the fixing module 20 may include a stretchable fabric such that the fixing module 20 may be warm as clothing. The first connecting portion 124 may rotatably connect the first binding portion 122 to the first central portion 110. For example, the first connecting portion 124 may be a ring or a hinge.

The first rear extending portion 130 may extend from the first central portion 110 to cover at least a portion of the rear surface of the user. The first rear extending portion 130 may extend toward an opposite side of the first front extending portion 120 based on the first central portion 110. The first rear extending portion 130 may be disposed on the opposite side of the first front extending portion 120 based on the user. The first rear extending portion 130 may be provided to be detachable from the second side frame 200.

The first rear extending portion 130 includes a first guide portion 132. The first guide portion 132 may guide the second side frame 200 to slide with respect to the first rear extending portion 130. The first guide portion 132 may be a slot provided lengthwise in an extending direction of the first rear extending portion 130. In this example, the first guide portion 132 may be referred to as a "guide slot". A plurality of first guide portions 132 may be provided. The plurality of first guide portions 132 may be provided in parallel. The fastening member 300 may be connected to the first guide portion 132.

Although FIG. 3 illustrates a manual adjustment of the distance between the first side frame 100 and the second side frame 200, in other example embodiments the distance between the first side frame 100 and the second side frame 200 may be electronically adjusted. For example, in other example embodiments, the fixing module 20 may include a motor (not shown). The first and second side frames may be connected in a rack and pinion design such that, in response to instructions generated by a controller (not shown), the motor generates a force that causes the pinion to rotate on the rack and adjust the distance between the first side frame 100 and the second side frame 200.

The controller (not shown) may include a processor and a memory storing computer readable code, that when executed by the processor, configures the controller as a special purpose computer that is configured to control the motion assistance apparatus 10.

The first side frame 100 may further include a first supporting member 140. The first supporting member 140 may include one or more of a first upper supporting member 142 and a first lower supporting member 144. The first supporting member 140 may stabilize the fixing member 20 when a force is applied thereto. Further, in some example embodiments, the first supporting member 140 may further include an internal pad (not shown) to further stabilize the fixing member 20 and also provide comfort to the user.

The first upper supporting member 142 may extend from the first rear extending portion 130 in an upward direction to support a lower back of the user. The first side supporting member 142 may extend in a direction orthogonal to a longitudinal direction of the first rear extending portion 130. For example, the first upper supporting member 142 may support a dorsal portion of the user. The first upper supporting member 142 may extend from the first rear extending portion 130 to a portion corresponding to about a midpoint of the dorsal portion of the user. As illustrated in FIG. 3, the first upper supporting member 142 may include a first extension 141 whose width increases in a direction of the first rear extending portion 130 near the waist of the user.

The first lower supporting member 144 may extend from the first rear extending portion 130 in a downward direction to support a lower side of the user. The first lower supporting member 144 may extend in a direction orthogonal to the longitudinal direction of the first rear extending portion 130. For example, the first lower supporting member 144 may support a hip portion of the user.

The first side frame 100 may include a reinforcing material (not shown), for example a pad, on an interior surface thereof. The reinforcing material may stabilize the fixing member 20 and also provide comfort to the user.

The second side frame 200 may be provided in a shape symmetrical to the first side frame 100. Hereinafter, the same names may be used to describe the elements included in the first side frame 100 described above and elements having common functions. Unless otherwise mentioned, the descriptions on the first side frame 100 may be applicable to the second side frames 200.

The second side frame 200 may cover a remaining portion of the waist of the user yet to be covered by the first side frame 100. The second side frame 200 may covering another side of the waist of the user, a remaining portion of the front surface of the waist user, and a remaining portion of the rear portion of the waist of the user. At least a portion of the second side frame 200 may overlap the first side frame 100. The second side frame 200 may include a second central portion 210, a second front extending portion 220, and a second rear extending portion 230.

The second central portion 210 may include a curved surface corresponding to one of the side surfaces of the waist of the user, and configured to attach to this side surface of the waist of the user. The second central portion 210 may be disposed to face the first central portion 110. The second central portion 210 may include a joint mounting portion 215 configured to extend toward a hip joint portion of the user. The joint mounting portion 215 may be provided to cover the hip joint portion.

The second front extending portion 220 may extend from the second central portion 210 to cover at least a portion of the front surface of the waist of the user. The second front extending portion 220 may be provided to be detachable from the first binding portion 122. For example, the second front extending portion 220 includes a second binding portion 222, and a second connecting portion 224.

The second binding portion 222 may be provided to be detachable from the first binding portion 122. For example, the second binding portion 222 may include a hook and loop fastener corresponding to the first binding portion 122. The second binding portion 222 may also be provided in a structure of a buckle corresponding to the first binding portion 122.

The second connecting portion 224 may rotatably connect the second binding portion 222 to the second central portion 210.

The second rear extending portion 230 may extend from the second central portion 210 to cover at least a portion of the rear surface of the user. The second rear extending portion 230 may extend towards an opposite side of the second front extending portion 220 based on the second central portion 210. The second rear extending portion 230 may be disposed on the opposite sides of the second front extending portion 220 based on the user. The second rear extending portion 230 may be provided to be detachable from the first rear extending portion 130.

The second rear extending portion 230 may include a second guide portion 232. The second guide portion 232 may guide the first rear extending portion 130 to slide with respect to the second rear extending portion 230. The second guide portion 232 may be a slot provided lengthwise in an extending direction of the second rear extending portion 230. The second guide portion 232 may be provided in a shape corresponding to the first guide portion 132. When the second rear extending portion 230 overlap the first rear extending portion 130, the second guide portion 232 may overlap at least a portion of the first guide portion 132. The fastening member 300 may be connected to the overlapping portion between the second guide portion 232 and the first guide portion 132. The fastening member 300 may fasten the second rear extending portion 230 with the first rear extending portion 130.

The second side frame 200 may further include a second supporting member 240. The second supporting member 240 may stabilize the fixing member 20 when a force is applied thereto. Further, in some example embodiments, the second supporting member 240 may further include an internal pad (not shown) to further stabilize the fixing member 20 and also provide comfort to the user.

The second supporting member 240 includes a second upper supporting member 242, and a second lower supporting member 244. While FIG. 4 illustrates that both the first side frame 100 and the second side frame 200 each include a supporting member 140, 240, in other example embodiments, only one of the first side frame 100 and the second side frame 200 may include a supporting member. For example, a single supporting member may be attached to one of the side frames in relatively closer contact to the user when the two side frames 100, 200 overlap around the user.

The second upper supporting member 242 may be provided in a shape symmetrical to the first upper supporting member 142. The second upper supporting member 242 may include a second extension 241. The second upper supporting member 242 and the first upper supporting member 142 may be disposed on both sides based on a spine of the user, respectively, to support erector spinae muscles of the user.

The second lower supporting member 244 may be provided in a shape symmetrical to the first lower supporting member 144. The second lower supporting member 244 and the first lower supporting member 144 may be disposed to support hip muscles of the user.

The second side frame 200 may include a reinforcing material (not shown), for example a pad, on an interior surface thereof. The reinforcing material may stabilize the fixing member 20 and also provide comfort to the user.

The fastening member 300 may fasten the first side frame 100 with the second side frame 200. The fastening member 300 may penetrate through the first guide portion 132 and the second guide portion 232, and prevent relative movements of the first rear extending portion 130 and the second rear extending portion 230. In an example, the fastening member 300 may include a bolt and a nut configured to pressurize the first rear extending portion 130 and the second rear extending portion 230 simultaneously. In an example, one of the first guide portion 132 or the second guide portion 232 may be provided in a form of a threaded hole, and the fastening member 300 may be a bolt having threads corresponding to the hole.

Hereinafter, the same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 5:
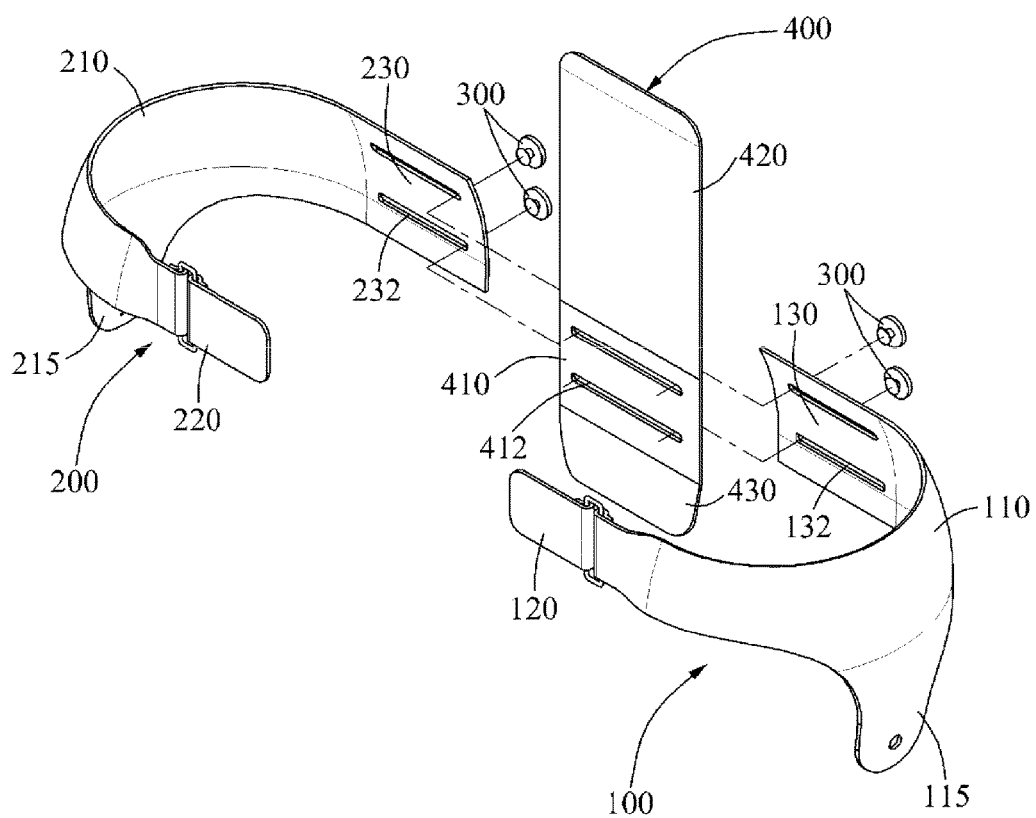
FIG. 5 is an exploded perspective view illustrating a fixing module according to some example embodiments.

FIG. 5 is an exploded perspective view illustrating a fixing module according to some example embodiments.

Referring to FIG. 5, the fixing module 20 may include the first side frame 100, the second side frame 200, the fastening member 300, and a supporting member 400. The supporting member 400 may include a fixing portion 410, an upper supporting member 420, and a lower supporting member 430.

The fixing portion 410 may overlap the first side frame 100 and the second side frame 200. The first rear extending portion 130 may be fixed to one side of the fixing portion 410, and the second rear extending portion 230 may be fixed to another side of the fixing portion 410. A third guide portion 412 may be provided in the fixing portion 410. The third guide portion 412 may be provided in a shape corresponding to the first guide portion 132 and the second guide portion 232.

The upper supporting member 420 may extend from the fixing portion 410 in an upward direction to support an upper side of the user. The upper supporting member 420 may extend in a direction orthogonal to a longitudinal direction of the fixing portion 410. For example, the upper supporting member 420 may support a dorsal portion of the user. The upper supporting member 420 may extend from the fixing portion 410 to a portion corresponding to a midpoint of the dorsal portion of the user.

The lower supporting member 430 may extend from the fixing portion 410 in a downward direction to support a lower side of the user. The lower supporting member 430 may extend in a direction orthogonal to the longitudinal direction of the fixing portion 410. For example, the lower supporting member 430 may support a hip portion of the user.

The fastening member 300 may include a first fastening member configured to fasten the first rear extending portion 130 with the fixing portion 410, and a second fastening member configured to fasten the second rear extending portion 230 with the fixing portion 410. While FIG. 5 illustrates two fastening members, the number of fastening members may vary. For example, in other example embodiments a single fastening member may be used to fasten the first rear extending portion 130 and the second rear extending portion 230 with the fixing portion 410.

Figure 6:
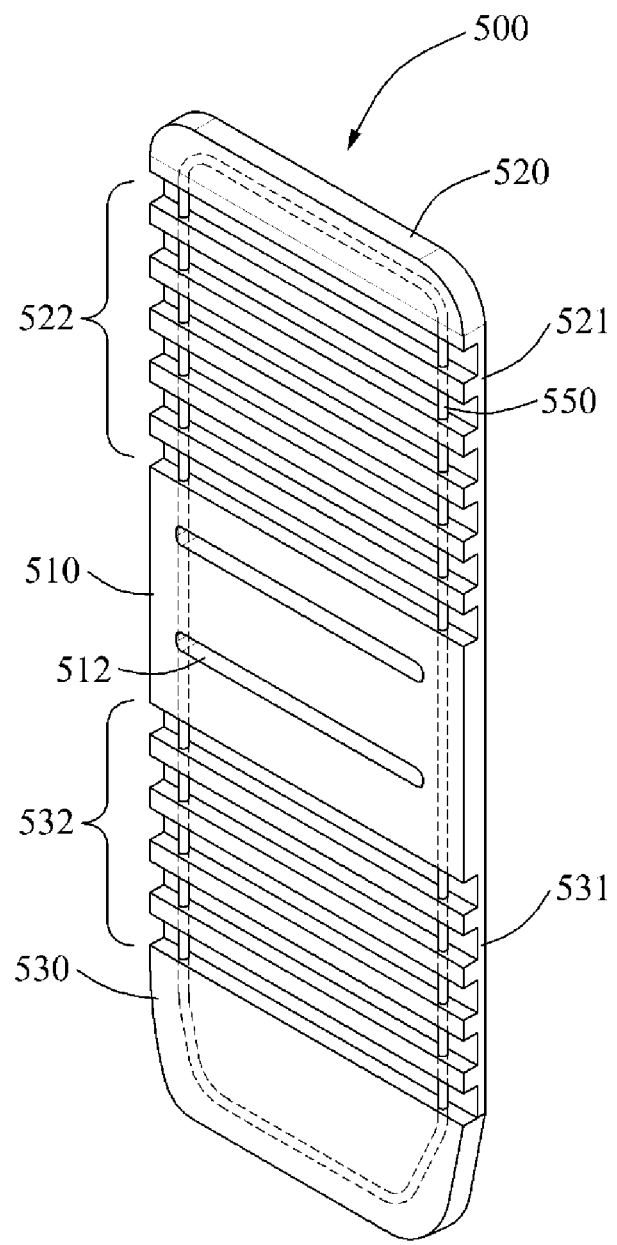
FIG. 6 is a perspective view illustrating a supporting member according to some example embodiments.

FIG. 6 is a perspective view illustrating a supporting member according to some example embodiments.

Referring to FIG. 6, in some example embodiments a supporting member 500 may be applicable to at least one of the supporting members described above to provide increased flexibility in a central portion and increased stiffness in an end portion thereof.

The supporting member 500 may include a fixing portion 510 in which a guide portion 512 is provided, an upper supporting member 520, a lower supporting member 530, and a stiffening device 550.

The upper supporting member 520 includes an upper plate 521 provided in a shape of a board extending from the fixing portion 510 in an upward direction, and a plurality of upper protruding portions 522 configured to protrude from the upper plate 521 such that the upper plate 521 is ribbed. The plurality of upper protruding portions 522 may be disposed to be spaced apart from each other in a longitudinal direction of the upper plate 521. The plurality of upper protruding portions 522 may be disposed in parallel. Through the foregoing structure, a flexibility of a central area of the upper supporting member 520 may increase.

The lower supporting member 530 may include a lower plate 531 provided in a shape of a board extending from the fixing portion 510 in a downward direction, and a plurality of lower protruding portions 532 configured to protrude from the lower plate 531 such that the lower plate 531 is ribbed. The plurality of lower protruding portions 532 may be disposed to be spaced apart from each other in a longitudinal direction of the lower plate 531. The plurality of lower protruding portions 532 may be disposed in parallel. Through the foregoing structure, a flexibility of a central area of the lower supporting member 530 may increase.

The stiffening device 550 may reinforce a stiffness of the upper supporting member 520 or the lower supporting member 530. For example, the stiffener 550 may increase a stiffness of both end portions of the upper supporting member 520 or the lower supporting member 530 to be greater than a stiffness of the central area of the upper supporting member 520 or the lower supporting member 530. The stiffener 550 may be disposed to penetrate through the plurality of upper protruding portions 522 and the plurality of lower protruding portions 532. The stiffening device 550 may be embedded in width directions of the upper plate 521 and the lower plate 531, and extend in longitudinal directions of the upper plate 521 and the lower plate 531. The stiffening device 550 may be a linear material such as, for example, a wire. The ends of the stiffening device 550 may be fixed to the ends of the upper plate 521 and/or the lower plate 531, and a center portion of the stiffening device 550 may be unfixed from a central portion of the upper plate 521 and/or the lower plate 531.

Figure 7:
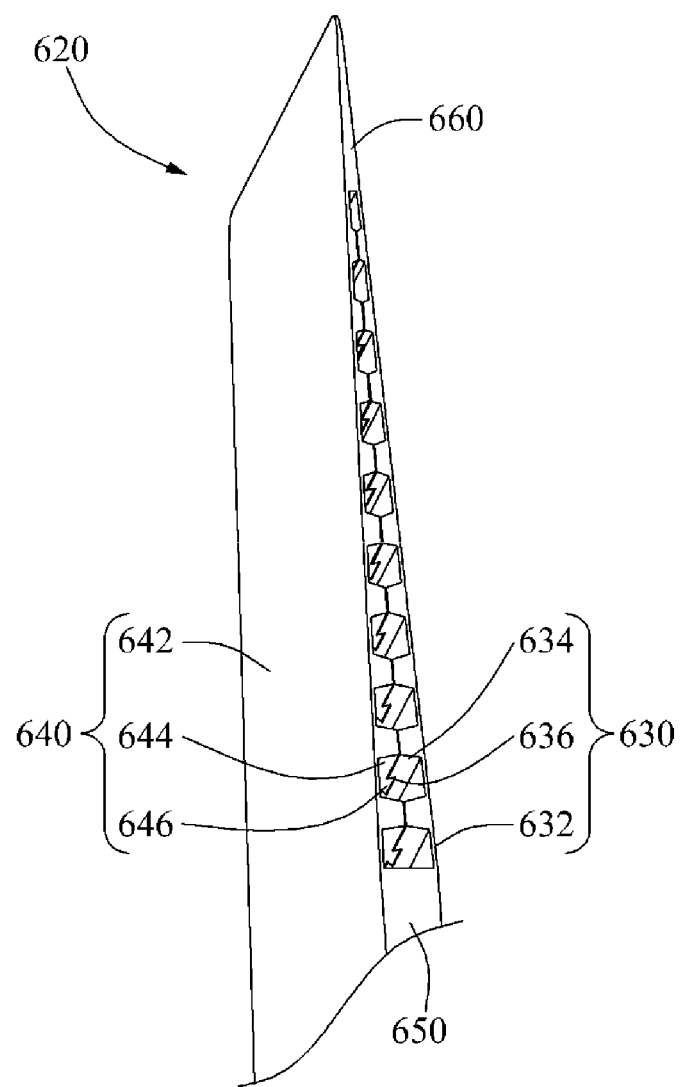
FIG. 7 is a perspective view illustrating a supporting member according to some example embodiments.

FIG. 7 is a perspective view illustrating a supporting member according to example embodiments.

Referring to FIG. 7, a supporting member 620 may be applicable to at least one of the upper supporting member and the lower supporting member described above to provide increased flexibility in a central portion and increased stiffness in the end portions thereof.

The supporting member 620 may include a first frame 630, a second frame 640, a connecting end portion 650, and an applying end portion 660.

The first frame 630 may include a first plate 632, a first protruding portion 634, and a first hanging portion 636.

The first plate 632 may be formed using a thin elastic board, for example, a material such as plastic, and steel.

The first protruding portion 634 may protrude from the first plate 632 toward the second frame 640. A plurality of first protruding portions 634 may be disposed to be spaced apart from each other in a longitudinal direction of the first plate 632. The first protruding portion 634 may be provided lengthwise in a direction orthogonal to the longitudinal direction of the first plate 632. A cross-section area of the first protruding portion 634 may decrease as a distance from the first plate 632 increases. A width of an upper side of the first protruding portion 634 may be smaller than a width of a lower side of the first protruding portion 634. The first protruding portion 634 may have an inclined surface in a shape of a taper. Through the foregoing structure, in a case in which a second protruding portion 644 is inserted into a space between two adjacent first protruding portions 634, the second protruding portion 644 may move along inclined surface without being obstructed by the first protruding portions 634.

The first hanging portion 636 may prevent a separation of the second frame 640 from the first frame 630. The first hanging portion 636 may be provided in a form of a groove including side surfaces of the first protruding portion 634 and an inner surface of the first plate 632. As shown in FIG. 7, the first hanging portion 636 may be provided in a form of a trapezoidal groove. To have a form of such a groove, a side surface of the first protruding portion 634 may protrude toward an inner side as a distance from the first plate 632 increases. For example, when first protruding portions 634 are arranged in two rows along both edges of the first plate 632, side surfaces of the first protruding portions 634 may be provided to protrude toward a center as a distance from the first plate 632 increases. These side surfaces of the first protruding portions 634 and the inner surface of the first plate 632 may be combined with a second hanging portion 646 of the second frame 640 to form a groove that prevents a separation.

The second frame 640 may be provided in a shape corresponding to the first frame 630. The second frame 640 includes a second plate 642, the second protruding portion 644, and the second hanging portion 646.

The second plate 642 may be provided in a shape corresponding to the first plate 632, and disposed to be spaced apart from the first plate 632. The second plate 642 may be formed using a thin elastic board, for example, a material such as plastic, and steel.

A space between the second plate 642 and the first plate 632 may increases from the applying end portion 660 toward the connecting end portion 650. A distance between the second plate 642 and the first plate 632 may increase as a distance from the applying end portion 660 increases.

The second protruding portion 644 may protrude from the second plate 642 toward the first plate 632. A plurality of second protruding portions 644 may be disposed to be spaced apart from each other in a longitudinal direction of the second plate 642. The second protruding portion 644 may be provided lengthwise in a direction orthogonal to the longitudinal direction of the second plate 642.

The second hanging portion 646 may prevent a separation of the first frame 630 from the second frame 640. As shown in FIG. 7, a cross-section of the second hanging portion 646 may be provided in a shape of a reversed trapezoidal dove tail. The second hanging portion 646, of which a width increases from the second plate 642 toward the first plate 632, may be combined with the first hanging portion 636 provided in a trapezoidal shape to prevent a separation of the second plate 642.

The connecting end portion 650 may be connected to the first rear extending portion 130 or the second rear extending portion 230 of FIGS. 1 through 4, or the fixing portion 410 of FIG. 5.

The applying end portion 660 may apply force to a user to offset a torsional moment when the torsional moment is applied to the fixing module 20 due to a reaction resulting from rotation of the joint assembly 40. The applying end portion 660 may apply force to an upper side or a lower side of the user, for example, a back or hips. Thus, the torsional moment resulting from the rotation of the joint assembly 40 and a torsional moment resulting from force received by the applying end portion 660 from the user may cancel each other out, whereby deformation of the fixing module 20 may be prevented. Dissimilar to the drawings, a thickness of the applying end portion 660 may be set to be greater than a sum of a thickness of the first frame 630 adjacent to the applying end portion 660 and a thickness of the second frame 640 adjacent to the applying end portion 660.

By the connecting end portion 650 and the applying end portion 660, end portions of a power transmitting frame, for example, the first side frame 100, to which both end portions of the first frame 630 and the second frame 640 are fixed, respectively, may have a relatively great stiffness resistant to a torsion. Dissimilar to both end portions restricted by each other, a central portion of the first frame 630 may relatively move with respect to a central portion of the second frame 640. Thus, a central portion of the power transmitting frame, for example, the first side frame 100 may have a greater flexibility than an end portion thereof. Conversely, a stiffness of both end portions of the power transmitting frame, for example, the first side frame 100 may be greater than a stiffness of a central portion thereof.

Through an interaction between the first hanging portion 636 and the second hanging portion 646, a separation between the first frame 630 and the second frame 640 may be prevented. Thus, the central portion of the first frame 630 may slide with respect to the central portion of the second frame 640. Thus, the power transmitting frame, for example, the first side frame 100 may prevent buckling of the first frame 630 or the second frame 640 while maintaining a flexibility of the central portion of the first frame 630 or the second frame 640.

Figure 8A:
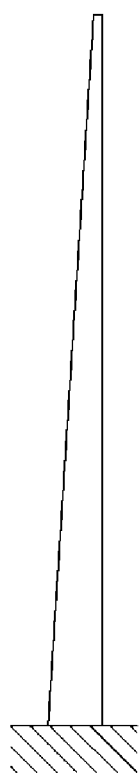
FIGS. 8A through 8C illustrate a supporting member deformed when an external force is applied to the supporting member according to some example embodiments.
Figure 8B:
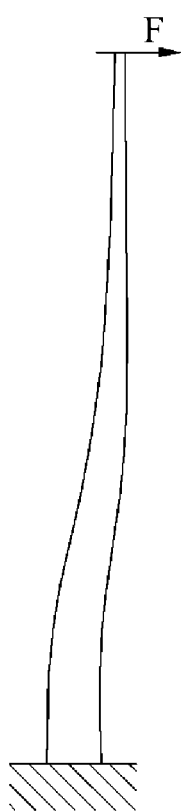
Figure 8C:
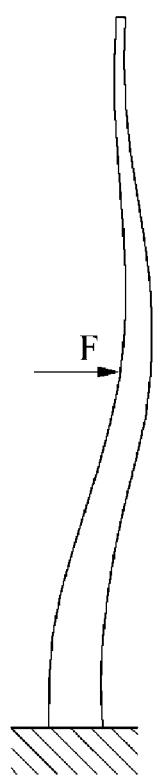

FIGS. 8A through 8C illustrate a supporting member deformed when an external force is applied to the supporting member according to example embodiments.

In detail, FIG. 8A illustrates a state in which a load is not applied to the supporting member, FIG. 8B illustrates a state in which a load F is applied to an end portion of the supporting member, and FIG. 8C illustrates a state in which a load F is applied to a central portion of the supporting module.

As described above, a stiffness of an end portion of the supporting member may be greater than a stiffness of the central portion thereof. Thus, as shown in FIG. 8B, when the load F is applied to the end portion of the supporting member, the end portion of the supporting member may resist the load F and thus may not experience little deformation. However, as shown in FIG. 8C, when the identical load F is applied to the central portion of the supporting member, due to the flexibility of the central portion of the supporting member, the central portion may experience greater deformation.

A conventional longitudinal member made of a flexible material may be weaker as a distance from a fixing end increases. Thus, force may not be transmitted properly at an end portion of the longitudinal member including the flexible material. Furthermore, a conventional longitudinal member may instead be made from a stiff material to transmit force properly at an end portion thereof. However, a flexibility of the longitudinal member including the stiff material may decrease at a central portion thereof. Thus, the longitudinal member including the stiff material may have difficulty in handling changes in a volume of a user with respect to various motion states. In this example, a frictional force with the user may increase.

In contrast, in one or more example embodiments, a supporting member may include a flexible central portion and a stiff end portion and thus, the supporting member may apply sufficient supporting force corresponding to a reaction resulting from rotation of the joint assembly 40 while reducing frictional force with the user.

Figure 9:
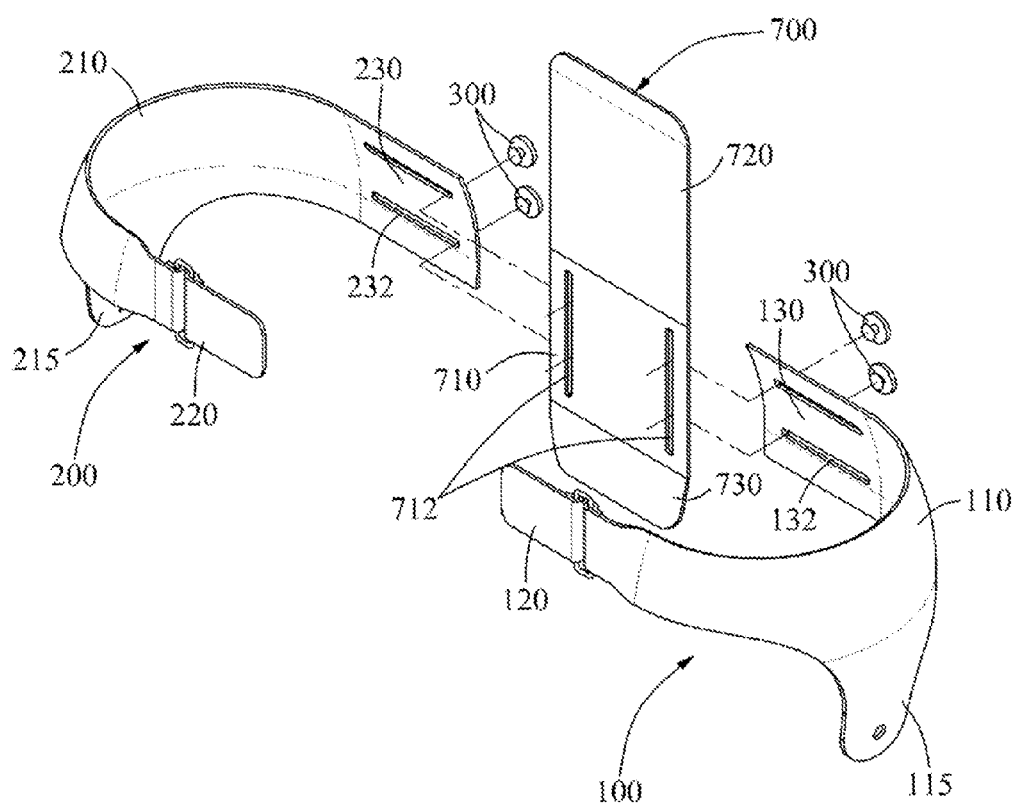
FIG. 9 is an exploded perspective view illustrating a fixing module according to some example embodiments.

FIG. 9 is an exploded perspective view illustrating a fixing module according to some example embodiments.

Referring to FIG. 9, the fixing module 20 may include the first side frame 100, the second side frame 200, the fastening member 300, and a supporting member 700 that is adjustable.

For example, the supporting member 700 may include a fixing portion 710, an upper supporting member 720, and a lower supporting member 730.

The fixing portion 710 may overlap the first side frame 100 and the second side frame 200. The first rear extending portion 130 may be fixed to one side of the fixing portion 710, and the second rear extending portion 230 may be fixed to another side of the fixing portion 710. A third guide portion 712 may be provided in the fixing portion 710.

The third guide portion 712 may include one or more slots provided in a direction perpendicular to the first guide portion 132 of the first side frame 100 and the second guide portion 232 of the second side frame 200. For example, the third guide portion 712 may include two parallel slots that extend in a direction perpendicular to the first and second guide portions 132, 232. By the third guide portion 712, a position of the supporting member 700 may be adjusted in a vertical direction with respect to the first side frame 100 or the second side frame 200.

The fastening member 300 may include a first fastening member configured to fasten the first rear extending portion 130 with the fixing portion 710, and a second fastening member configured to fasten the second rear extending portion 230 with the fixing portion 710. While FIG. 9 illustrates two fastening members, the number of fastening members may vary. For example, in other example embodiments a single fastening member may be used to fasten the first rear extending portion 130 and the second rear extending portion 230 with the fixing portion 710.

A number of example embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A fixing device comprising:
   a first side frame including a first central portion configured to attach to one side of a user, a first front extending portion configured to extend from the first central portion along a front side of the user, and a first rear extending portion configured to extend from the first central portion along a rear side of the user;
   a second side frame including a second central portion configured to attach to another side of the user such that the second central portion faces the first central portion and is separated from the first central portion by a distance with a portion of user enclosed therebetween, a second front extending portion configured to extend from the second central portion along the front side of the user, and a second rear extending portion configured to extend from the second central portion along the rear side of the user; and
   a supporting device extending from one or more of the first rear extending portion and the second rear extending portion, the supporting device configured to support an area of the rear side of the user such that the area supported by the supporting device varies when the distance between the first central portion and the second central portion is adjusted, wherein
      the first front extending portion and the second front extending portion are configured to overlap around the front side of the user in a front overlapping area that is adjustable, and
      the first rear extending portion and the second rear extending portion are configured to overlap around the rear side of the user in a rear overlapping area that is adjustable.

2. The fixing device of claim 1, wherein the first front extending portion is configured to detach from the second front extending portion, and
   the first rear extending portion is configured to detach from the second rear extending portion.

3. The fixing device of claim 2, wherein the first front extending portion comprises:
   a binding portion configured to bind to the second front extending portion; and
   a connecting portion configured to rotatably connect the binding portion to the first central portion.

4. The fixing device of claim 2, wherein the first rear extending portion is configured to slide with respect to the second rear extending portion.

5. The fixing device of claim 4, wherein the first rear extending portion includes a first guide hole therethrough and the second rear extending portion includes a second guide hole corresponding to the first guide hole, and the fixing device further comprising:
   a fastening member configured to penetrate through the first guide hole and the second guide hole to prevent relative movements of the first rear extending portion and the second rear extending portion.

6. The fixing device of claim 1, wherein the supporting device is configured to extend from a rear extending portion of at least one of the first side frame and the second side frame in a direction orthogonal to a longitudinal direction of the rear extending portion such that a position of the supporting device relative to the rear side of the user is configured to move with the at least one of the first side frame and the second side frame when the distance between the first central portion and the second central portion is adjusted by varying an adjustable amount of overlap between the first rear extending portion and the second rear extending portion.

7. The fixing device of claim 6, wherein the supporting device comprises:
   a plate orthogonal to the longitudinal direction of the rear extending portion; and
   a plurality of protruding portions configured to protrude from the plate.

8. The fixing device of claim 7, wherein the plurality of protruding portions are spaced apart from one another in a longitudinal direction of the plate.

9. The fixing device of claim 8, wherein the supporting device further comprises:
a stiffening device configured to penetrate through the plurality of protruding portions to stiffen ends of the supporting device.

10. The fixing device of claim 6, wherein the supporting device comprises:
a plate orthogonal to the longitudinal direction of the rear extending portion, the plate having end portions and a central portion; and
a stiffening device configured to attach to the plate such that the stiffening device is fixed to the end portions of the plate and unfixed from the central portion.

11. The fixing device of claim 6, wherein the supporting device comprises:
a plate orthogonal to the longitudinal direction of the rear extending portion; and
a stiffening wire configured to be embedded at an end portion of the plate in a width direction of the plate, and to extend in a longitudinal direction of the plate.

12. The fixing device of claim 6, wherein the supporting device is configured to have a length longer than a width, and
a stiffness of both end portions of the supporting device is greater than a stiffness of a central area of the supporting device in a longitudinal direction of the supporting device.

13. The fixing device of claim 1,
wherein the supporting device comprises:
a first upper supporting member configured to extend from the first rear extending portion in a cranial direction, and
a second upper supporting member configured to extend from the second rear extending portion in the cranial direction, and
wherein the first upper supporting member and the second upper supporting member are configured to extend to both sides of a spine of the user to support erector spinae muscles of the user.

14. The fixing device of claim 1, wherein the supporting device comprises:
a first lower supporting member configured to extend from the first rear extending portion in a caudal direction to support muscles in a first hip of the user, and
a second lower supporting member configured to extend from the second rear extending portion in the caudal direction to support muscles in a second hip of the user.

15. The fixing device of claim 1, wherein the supporting device comprises:
a pair of supporting devices including a first supporting device and a second supporting device extending from the first rear extending portion and the second rear extending portion, respectively, in a direction orthogonal to a longitudinal direction thereof, wherein
the area of the rear side of the user supported by the pair of supporting devices varies when the distance between the first central portion and the second central portion is adjusted by varying an adjustable amount of overlap between the first rear extending portion and the second rear extending portion.

16. A fixing device comprising:
a first side frame configured to cover a first side surface of a user, the first side frame having two end portions that are configured to extend along a front surface and a rear surface of the user;
a second side frame configured to cover a second side surface of the user, the second side frame having two end portions that are configured to extend along the front surface and the rear surface of the user; and
a supporting device configured to slidably connect the first side frame and the second side frame, and to support the rear surface of the user, wherein
the first side frame and the second side frame are configured to overlap around a front side of the user in an front overlapping area that is adjustable, and
the first side frame and the second side frame are configured to overlap around a rear side of the user in a rear overlapping area that is adjustable.

17. The fixing device of claim 16, wherein the two end portions of the first side frame are configured to detach from corresponding ones of the two end portions of the second side frame.

18. A motion assistance apparatus comprising:
a fixing device including a first separable frame configured to mount on a first side surface of a user, a second separable frame configured to mount on a second side surface of the user, and a supporting device, the first separable frame and the second separable frame including a first rear extending portion and a second rear extending portion, respectively, and the supporting device extending from one or more of the first rear extending portion of the first separable frame and the second rear extending portion of the second separable frame, the supporting device configured to support an area of a rear side of the user such that the area supported by the supporting device varies when a distance between the first separable frame and the second separable frame is adjusted;
a driving module attached to the fixing device; and
a joint assembly configured to rotate by the driving module to assist a rotary motion of at least one joint of the user, wherein
the first separable frame and the second separable frame are configured to overlap around the first side surface of the user in a front overlapping area that is adjustable, and
the first separable frame and the second separable frame are configured to overlap around the second side surface of the user in a rear overlapping area that is adjustable.

19. The motion assistance apparatus of claim 18, wherein the first separable frame and the second separable frame include a flexible material, and the supporting device comprises:
an upper supporting member and a lower supporting member configured to extend toward an upper side and a lower side of the user, respectively, the upper supporting member configured to provide pressure to the upper side of the user when the joint assembly rotates in a first direction, and the lower supporting member configured to provide pressure to the lower side of the user when the joint assembly rotates in a second direction different from the first direction.

20. The motion assistance apparatus of claim 19, wherein the supporting device comprises:
a pair of supporting devices including a first supporting device and a second supporting device extending from the first rear extending portion and the second rear extending portion, respectively, in a direction orthogonal to a longitudinal direction of the first separable frame and the second separable frame, wherein the area of the rear side of the user supported by the pair of supporting devices varies when the distance between the first separable frame and the second separable frame is adjusted by varying an adjustable amount of overlap therebetween.

21. A motion assistance apparatus comprising:

a fixing device configured to attach to a waist of a wearer thereof, the fixing device including a plurality of interlocking frames separated by a distance and a supporting device, each of the plurality of interlocking frames including a rear portion, and the supporting device extending from the rear portion of one or more of the plurality of interlocking frames, the supporting device configured to support an area of a lower back of the wearer such that the area supported by the supporting device varies when the fixing device adjusts the distance between the plurality of interlocking frames to secure the motion assistance apparatus onto the waist of the wearer;

a plurality of attachment devices configured to attach to thighs of the wearer; and a plurality of joint assemblies mounted to respective ones of the plurality of interlocking frames, the joint assemblies configured to apply a torque to the plurality of attachment devices to assist the wearer with movement of their hip joints, wherein the plurality of interlocking frames includes a first interlocking frame and a second interlocking frame, the first interlocking frame and the second interlocking frame are configured to overlap around a front side of the wearer in an front overlapping area that is adjustable, and the first interlocking frame and the second interlocking frame are configured to overlap around a rear side of the wearer in a rear overlapping area that is adjustable.

22. The motion assistance apparatus of claim 21, the first interlocking frame is configured detach from the second interlocking frame to allow the wearer to remove the fixing device.

23. The motion assistance apparatus of claim 21, wherein the rear portions configured to contact a respective side of the lower back of the wearer, the plurality of interlocking frames further includes front portions configured to contact a respective side of a lower abdomen of the wearer, and a first one of the rear portions and the front portions of the plurality of interlocking frames is configured to allow a fastening member to penetrate through a guide slot therein to allow a first one of the plurality of interlocking frames to slide relative to a second one of the plurality of interlocking frames; and a second one of the rear portions and the front portions of the plurality of interlocking frames include a clasp configured to selectively fasten the first interlocking frame to the second interlocking frame.

24. The motion assistance apparatus of claim 21, wherein the supporting device is configured to extend in one or more of a cranial or caudal direction from the fixing device to offset a torsional force generated when the plurality of joint assemblies applies the torque to the attachment devices.

25. The motion assistance apparatus of claim 24, wherein the supporting device has a shape such that a stiffness of the supporting device increases towards distal ends thereof.

26. The motion assistance apparatus of claim 24, wherein the fixing device is configured to adjust the distance between the plurality of interlocking frames in a first direction and move the supporting device in a second direction perpendicular to the first direction.

27. The motion assistance apparatus of claim 24, wherein the plurality of interlocking frames are symmetric with respect to the supporting device.

28. The motion assistance apparatus of claim 21, wherein the supporting device comprises:

a pair of supporting devices including a first supporting device and a second supporting device extending from the rear portion the first interlocking frame and the second interlocking frame, respectively, in a direction orthogonal to a longitudinal direction of the plurality of interlocking frames, wherein the area of the lower back of the wearer supported by the pair of supporting devices varies when the distance between the plurality of interlocking frames is adjusted by varying an adjustable amount of overlap therebetween.

* * * * *